United States Patent [19]

Adams et al.

[11] Patent Number: 4,740,588

[45] Date of Patent: Apr. 26, 1988

[54] NOVEL SUBSTRATE PEPTIDES

[75] Inventors: Steven P. Adams, St. Charles; Dwight A. Towler, St. Louis, both of Mo.; Luis Glaser, Miami, Fla.

[73] Assignee: Washington University, St. Louis, Mo.

[21] Appl. No.: 924,543

[22] Filed: Oct. 29, 1986

Related U.S. Application Data

[63] Continuation-in-part of Ser. No. 894,235, Aug. 7, 1986, abandoned.

[51] Int. Cl.$^4$ ................................................ C07K 7/06
[52] U.S. Cl. .................................... 530/328; 530/329; 530/330
[58] Field of Search ............... 530/328, 329, 330, 359; 514/16, 17

[56] References Cited

U.S. PATENT DOCUMENTS 4,320,118  3/1982  White et al. ........................ 530/317

OTHER PUBLICATIONS

Towler & Glaser, Proc. Natl. Acad. Sci. U.S.A. 83, 2812–2816 (1986).
Chem. Abstracts, vol. 93, (1980), 40461c.
Chem. Abstracts, vol. 94, (1981), 134981u.
Chem. Abstracts, vol. 97, (1982), 19650m.

*Primary Examiner*—Delbert R. Phillips
*Assistant Examiner*—Teresa D. Wessendorf
*Attorney, Agent, or Firm*—Scott J. Meyer; James W. Williams, Jr.

[57]  ABSTRACT

A peptide substrate for myristoylating enzymes is disclosed having an amino acid sequence selected from the group consisting of the following sequences or a physiologically acceptable amide or salt derivative thereof:

$$\overset{1}{\text{Gly}}-\text{R}-\text{S}-\text{T}-\overset{5}{\text{W}},$$

$$\overset{1}{\text{Gly}}-\text{R}-\text{S}-\text{T}-\text{W}-\overset{6}{\text{X}},$$

$$\overset{1}{\text{Gly}}-\text{R}-\text{S}-\text{T}-\text{W}-\text{X}-\overset{7}{\text{Y}} \text{ or}$$

$$\overset{1}{\text{Gly}}-\text{R}-\text{S}-\text{T}-\text{W}-\text{X}-\text{Y}-\overset{8}{\text{Z}},$$

wherein
R = Ala, Asn, Gln or Ser;
S = Ala, Arg, Gln, Glu, Phe or Ser;
T = Ala or Lys;
W = Ala or Ser;
X = Ala, Tyr, or Lys;
Y = Arg or Pro; and
Z = Arg, Leu or Lys.

11 Claims, No Drawings

NOVEL SUBSTRATE PEPTIDES

CROSS-REFERENCE TO RELATED APPLICATION

This is a continuation-in-part of copending application Ser. No. 894,235, filed Aug. 7, 1986, now abandoned.

BACKGROUND OF THE INVENTION

This invention relates to novel peptides and more particularly to unique peptides having from 5 to 8 amino acid residues which are useful as substrates of myristoylating enzymes.

Fatty acid acylation of specific eukaryotic proteins is a well established process which can conveniently be divided into two categories. On the one hand, palmitate ($C_{16}$) is linked to membrane proteins via ester or thioester linkage post-translationally, probably in the Golgi apparatus.

On the other hand, it is known that myristate ($C_{14}$) becomes covalently bound to soluble and membrane proteins via amide linkage early in the protein biosynthetic pathway. In the N-myristoylated proteins, amino-terminal glycine residues are known to be the site of acylation. See Aitkin et al., *FEBS Lett.* 150, 314–318 (1982); Schultz et al., *Science* 227, 427–429 (1985); Carr et al., *Proc. Natl. Acad. Sci. USA* 79, 6128–6131 (1982); Ozols et al., *J. Biol. Chem.* 259, 13349–13354 (1984); and Henderson et al., *Proc. Natl. Acad. Sci. USA* 80, 339–343 (1983).

The function of protein N-myristoylation is only beginning to be understood. Four of the known N-myristoyl proteins —$p60^{src}$, cyclic AMP-dependent protein kinase catalytic subunit, the calcineurin B-subunit, and the Murine Leukemia Virus oncogenic gag-abl fusion protein—are either protein kinases or a regulator of a phosphoprotein phosphatase (calcineurin) which modulate cellular metabolic processes. For $p60^{v-src}$, it has been shown that myristoylation is required for membrane association and expression of this protein's cell transforming potential. See Cross et al., *Molec. Cell. Biol.* 4, 1834–1842 (1984); Kamps et al., *Proc. Natl. Acad. Sci. USA* 82, 4625–4628 (1985).

The development of relatively short synthetic peptides which can be conveniently made by synthetic peptide synthesis would be highly desirable for identifying and in studying the regulation of enzyme action in fatty acid acylation. Such peptides could serve as synthetic substrates for the myristoylating enzyme in yeasts and mammalian cells. They could also serve as highly specific competitive inhibitors of the naturally-occurring substrates.

The myristoylation reaction can be represented as follows:

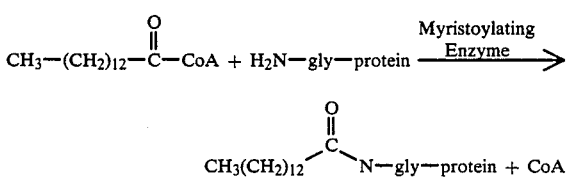

BRIEF DESCRIPTION OF THE INVENTION

In accordance with the present invention, novel peptide substrates for myristoylating enzymes are provided which have an amino acid sequence selected from the group consisting of the following sequences or a physiologically acceptable amide, or salt derivative thereof:

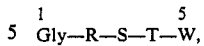

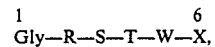

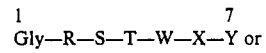

wherein
R=Ala, Asn, Gln or Ser;
S=Ala, Arg, Gln, Glu, Phe or Ser;
T=Ala or Lys;
W=Ala or Ser;
X=Ala, Tyr, or Lys;
Y=Arg or Pro; and
Z=Arg, Leu or Lys.

Illustrative examples of these peptide substrates are: pentapeptides such as Gly-Asn-Ala-Ala-Ser; hexapeptides such as Gly-Asn-Ala-Ala-Ala-Ala; heptapeptides such as Gly-Asn-Ala-Ala-Ala-Ala-Arg; and octapeptides such as

wherein R=Asn, Gln or Ser;

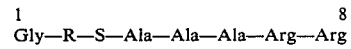

wherein
R=Ala or Asn and
S=Arg, Gln or Phe;
Gly-Asn-Glu-Ala-Ala-Ala-Arg-Arg;
Gly-Asn-Glu-Ala-Ser-Tyr-Pro-Leu; and
Gly-Ser-Ser-Lys-Ser-Lys-Pro-Lys.

Illustrative amide derivatives of these peptides are the carboxyamides. Illustrative salt derivatives are the HCl salts.

DETAILED DESCRIPTION OF THE INVENTION

The novel peptides of this invention can be made by appropriate adaptation of conventional methods for peptide synthesis. Thus, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxypthalimide or N-hydroxy-succinimide, and various cleavage reagents, e.g., trifluoracetic acid, HCL in dioxane, boron tris-(trifluoracetate) and cyanogen bromide, and reaction in solution with isolation and purification of intermediates is well-known classical peptide methodology.

Preferably, the peptides of this invention are prepared by the well-known Merrifield solid support method. See Merrifield, *J. Amer. Chem. Soc.* 85, 2149-54 (1963) and *Science* 150, 178-85 (1965). This procedure, though using many of the same chemical reactions and blocking groups of classical peptide synthesis, provides a growing peptide chain anchored by its carboxyl terminus to a solid support, usually cross-linked polystyrene or styrenedivinylbenzene copolymer. This method conveniently simplifies the number of procedural manipulations since removal of the excess reagents at each step is effected simply by washing of the polymer.

The general reaction sequence for conventional Merrifield peptide synthesis can be illustrated as follows:

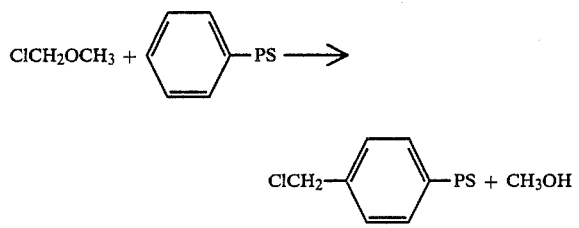

Chloromethylation step to provide reactive group for attachment of peptide, wherein PS = Polystyrene Residue.

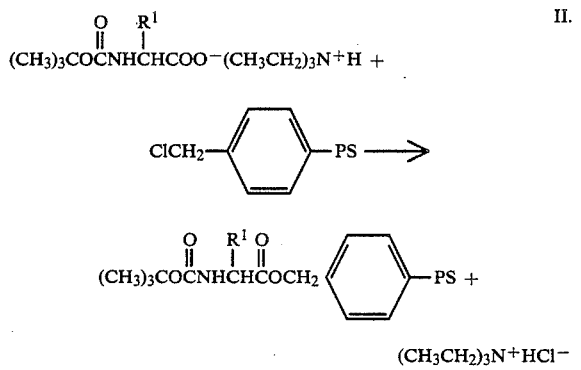

Esterification Step—Reaction with Triethylammonium salt of the First Protected amino Acid ($R_1$) Using t-BOC Protecting Group.

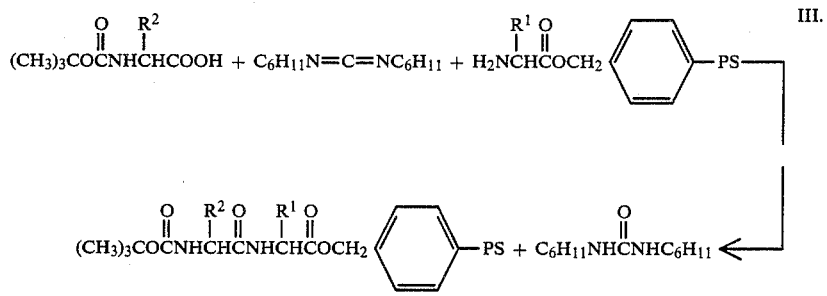

Peptide forming step with Dicyclohexylcarbodiimide Coupling Agent. This step III follows cleavage of t-BOC such as by treatment, for example, with 25% trifluoracetic acid in methylene chloride and liberation of N-terminal amine by excess of triethylamine, thereby enabling it S to react with the activated carboxyl of the next protected amino acid ($R^2$). A final step involves cleavage of the completed peptide from the PS resin such as by treatment, for example, with anhydrous HF in anisole.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology* 32, pp. 221-296, F. F. Nold, Ed., Interscience Publishers, New York, 1969; and Erickson and Merrifield, *The Proteins*, Vol. 2, p. 255 et seq. (ed. Neurath and Hill), Academic Press, New York, 1976.

The preferred peptide substrates of this invention are
Gly-Asn-Ala-Ala-Ala-Ala-Arg-Arg,
Gly-Asn-Phe-Ala-Ala-Ala-Arg-Arg,
Gly-Gln-Ala-Ala-Ala-Ala-Arg-Arg, and
Gly-Ser-Ser-Lys-Ser-Lys-Pro-Lys.

All these octapeptides have $K_m$s of 0.04 mM to 0.07 mM.

A most preferred peptide in accordance with the present invention is
Gly-Asn-Ala-Ala-Ala-Ala-Arg-Arg-NH$_2$.

The carboxy-terminal carboxamide form of the peptide as shown, above, is preferred to the carboxylate form of the peptide. The latter octapeptide contains the six amino-terminal residues of bovine cardiac muscle cAMP-dependent protein kinase, followed by two arginine residues which replace the lysine residue in the native N-terminal heptapeptide sequence reported by Carr et al., *Proc. Natl. Acad. Sci USA* 79, 6128–6131 (1982). The Carr heptapeptide was obtained as a blocked tryptic fragment upon proteolysis of a cyanogen bromide cleavage fragment of the native protein. Since the endogenous protein was already myristoylated, the peptide could not have been used as an in vitro acyl acceptor.

The synthetic octapeptide Gly-Asn-Ala-Ala-Ala-Ala-Arg-Arg was used to identify a unique enzymatic activity which transfers myristic acid to the amino terminal glycine of this and other peptides. The substrate activity of the novel peptides for the myristoylating enzyme is illustratively demonstrated with the N-myristoylglycylpeptide synthetase (N-myristoyl transferase) from *Saccharomyces cerevisiae*. The enzyme activity was determined in an in vitro assay which measures the transfer of [$^3$H]-myristic acid to the acceptor peptide.

The transfer reaction is dependent on adenosine triphosphate (ATP) and coenzyme A (CoA). The enzymatic product was then identified by high performance liquid chromatography (HPLC) by co-elution with a chemically synthesized myristoyl peptide standard. To demonstrate that the enzymatic reaction product and the chemically synthesized standard were identical and contained myristate covalently bound to glycine, HPLC-purified standards and enzymatic products were both digested with pronase and analyzed by reverse phase HPLC. Both contained M-myristoyl glycine.

The myristoylglycylpeptide synthetase enzyme exhibits very high specificity for myristoyl CoA as the acyl donor to the peptides of this invention. The glycine in the N-terminal amino acid position 1 of the peptide is critical to the activity of the substrate for this purpose; a peptide with alanine at this position does not function as a substrate for this enzyme. It has also been found that substitution with aspartic acid, tyrosine, phenylalanine, or with the D-asparagine stereoisomer instead of L-asparagine in amino acid position 2 results in inactive substrates. Likewise, those smaller or larger peptides having an N-terminal glycine which were tested were found to be inactive, namely:
Gly-Asn,
Gly-Pro-Arg-Pro, and
Gly-Ser-Ser-Lys-Ser-Pro-Lys-Arg-Pro-Ser.
The last peptide failed to be utilized as a substrate, and they all failed to inhibit myristoylation of the active peptide Gly-Asn-Ala-Ala-Ala-Ala-Arg-Arg.

A protease-deficient strain of *Saccharomyces cerevisiae*, JR153 [Hemmings et al., *Proc. Natl. Acad. Sci. USA* 78, 435–439 (1981)], was used as a source of N-myristoylglycylpeptide synthetase to illustratively demonstrate the acylation of the octapeptides. This strain was shown to contain endogenous N-myristoyl proteins by labeling yeast with [$^3$H]myristic acid followed by lysis of cells and analysis of cellular proteins by sodium dodecylsulfate polyacrylamide gel electrophoresis (SDS-PAGE). N-[$^3$H]myristoyl glycine could be isolated from labeled endogenous acyl proteins by digestion with pronase followed by separation and analysis by reversed phase HPLC.

N-myristoylating enzyme from BC$_3$H1 cells [a mouse muscle cell line described by Schubert et al., *J. Cell Biol.* 61, 398–413(1974)] was similarly used to illustratively demonstrate the acylation of the octapeptides by the N-myristoylating enzyme present in the cells of higher eukaryotes The following examples will illustrate the invention in greater detail although it will be understood that the invention is not limited to these specific examples.

EXAMPLE 1

All peptides herein were prepared essentially by the following method used for the peptide most preferred as a substrate A. Synthesis of Gly-Asn-Ala-Ala-Ala-Ala-Arg-Arg-NH$_2$.

The peptide was synthesized on p-methylbenzhydrylamine resin having a substitution of 0.35 mmol amino groups/gram of resin by the method of Merrifield [R. B. Merrifield, *J. Am. Chem. Soc.*, 85, 2149–2154 (1963)] BOC-protected amino acids (4 equivalents) were used to form symmetrical anhydrides by mixing a 2:1 ratio of BOC-amino acid and dicyclohexylcarbodiimide in dichloromethane for 15 minutes. The solvent was evaporated in vacuo and the anhydride was redissolved in dimethylformamide and mixed with the resin and agitated for 1 hour. In the reaction of asparagine (and glutamine and arginine), an equimolar amount of hydroxybenzotriazole (based on amino acid) was included in the reaction mixture. The BOC-protecting groups were removed using 50% trifluoroacetic acid (TFA) in dichloromethane and the resin was neutralized with 10% diisopropylethylamine in dimethylformamide prior to coupling of amino acids.

The peptide was removed from the resin and deprotected using liquid HF/anisole (9:1, V/v) at 0 degrees for one hour. The crude peptide was extracted from the resin with 50% aqueous acetic acid and lyophilized.

B. Purification

Crude peptide was dissolved in water and applied to a Waters $\mu$-Bondapak C$_{18}$ column (19 mm $\times$ 150 mm) and eluted with a gradient of 0–15% acetonitrile (0.05% TFA) in water (0.05% TFA) over 15 minutes at a flow rate of 9 ml/min. Fractions containing the product were combined and lyophilized, and the purity and identity of the peptide were ascertained by analytical HPLC and by amino acid analysis.

EXAMPLE 2

Labeling and extraction of Yeast protein for electrophoretic analysis. Yeast (*S. cerevisiae* strain JR153, mating type alpha, trp1, prb1, prc1, pep4-3) was grown to an optical density at 660 nm of 1 to 3 in a rotary shaker at 30° C. in YPD medium (1% yeast extract, 2% Bactopeptone, 2% dextrose in distilled water). Fifteen ml aliquots of yeast culture were labeled for 30 minutes under identical conditions by addition of 1 mCi of [$^3$H]fatty acid in 10 $\mu$l of ethanol. At the end of the labeling period, the cultures were cooled for five minutes on ice and the cells were pelleted at 4° C. by centrifugation at 7600$\times$g for 10 minutes. Cells were then resuspended in 1 ml of 10 mM NaN$_3$ in 140 mM NaCl/10 mM phosphate, pH 7.2, transferred to 1.5 ml polypropylene conical centrifuge tubes, and collected by centrifugation at 4° C. as above. The supernatant was discarded, and the cells were suspended in 100 $\mu$l of 5 mM Tris, pH 7.4, 3 mM dithiothreitol, 1% SDS, 1 mM phenylmethylsulfonylfluoride, and broken with one cell volume equivalent of 0.5 mm glass beads, by six 30 second spurts of vigorous vortexing with cooling on ice between each vortexing. Debris was removed by centrifugation for 30 seconds at 8000$\times$g in a tabletop Eppendorf centrifuge. The supernatant was then alkylated in 125 $\mu$l of 8 mM Tris, pH 8.0, with 20 mM iodoacetamide for 1 hour at room temperature. Twenty microliter aliquots were analyzed by conventional SDS-PAGE and fluorography methodology essentially as described by Olson et al., *J. Biol. Chem.* 259, 5364–5367 (1984).

Analysis of the linkage [$^3$H]fatty acids to proteins. Twenty microliters of the reduced and alkylated [$^3$H]fatty acid labeled yeast protein was treated with 7 $\mu$l of freshly prepared 4M hydroxylamine/20 mM glycine, pH 10. After treatment for hours at 23° C., samples were prepared for electrophoresis and fluorography as above.

To determine the hydroxylamine-stable linkage of [$^3$H]myristic acid to the 20,000 dalton acylprotein in JR153, the cultures were labeled as described above except that the cells were treated for 15 minutes prior to addition of fatty acid with 2 $\mu$g/ml cerulenin, a known inhibitor of yeast fatty acid synthesis which enhances the labeling of the specific acylproteins in JR153 several fold. Cellular protein was then prepared and separated by SDS 12% polyacrylamide gel electrophoresis as described above, running molecular weight prestained protein standards in gel lanes adjacent to sample lanes. After electrophoresis, 2 mm gel slices were cut from the undried gel sample lanes in the 20,000 dalton molecular weight region. Gel slices were rinsed rapidly with 0.5 ml of 10% methanol in water, then individually digested for 72 hours at 37° C. with 1 mM of Pronase E (Sigma, St. Louis, Mo.) in 1 ml of 50 mM ammonium bicarbonate, pH 7.9, with mixing on a Labquake mixer (Labindustries, Berkeley, Calif.). One microliter of toluene was added per digest to retard microbial growth. One mg of fresh Pronase E was added at 24 hours. Following digestion, the radioactivity present in aliquots of each digest was determined. The digest from the slice containing radioactivity was removed, the gel slice was rinsed once with 500 µl of 0.1% SDS, and the digest and rinse were combined and acidified to pH 1–2 with 40 µl of 6 N HCl. The acidified solution was extracted twice with 1.5 ml of chloroform-methanol (2:1, v/v). The combined organic phases were backwashed once with 1 ml of chloroform-methanol-0.01 N HCl (1:10:10, v/v/v), and the organic phase dried under a stream of nitrogen. The residue was redissolved in 50% methanol-50% HPLC buffer A (see below). Ninety-seven percent of the radioactivity present in the original protein digest was recovered after the extraction protocol. The sample was analyzed by reverse phase HPLC on a Waters µ-Bondapak $C_{18}$ column at a flow rate of 1 ml per min, using as buffer A, 0.1% trifluoroacetic acid/0.05% triethylamine in water, and as buffer B, 0.1% trifluoracetic acid in acetonitrile, eluting with a 1% per minute acetonitrile gradient. One minute fractions were collected, and radioactivity was determined by liquid scintillation counting. The myristoyl-[$^3$H]glycine standard was synthesized essentially as described by Towler and Glaser, *Biochemistry* 25, 878–884 (1986), and analyzed by HPLC as above.

Synthesis of fatty acyl peptide standards. The synthesis of acylpeptide standards was performed by reacting the radioactive symmetric myristic acid or palmitic acid anhydride with GlyAsnAlaAlaAlaAlaArgArg in pyridine. One hundred microcuries of [$^3$H]fatty acid was treated with 4 µl of the respective fatty acyl chloride, then suspended in 150 µl of pyridine containing 4.8 mg of the respective non-radioactive fatty acid. The reaction was allowed to proceed for 60 minutes at 23° C. Sixty-five microliters of this solution was then added to 400–500 µg of GlyAsnAlaAlaAlaAlaArgArg. The reaction was allowed to proceed overnight with mixing on a Labquake Mixer. The pyridine was then evaporated under vacuum, the residue extracted twice with 0.3 ml of petroleum ether, and redissolved in 400 µl of 50% methanol in water. The reaction products were then purified and analyzed by reverse phase HPLC as described above. The chemically synthesized standard and the enzymatic product were also both digested with Pronase E and analyzed by reverse phase HPLC as described above for the 20,000 dalton acylprotein, except that 200 µg of the protease was sufficient for complete digestion.

Preparation of yeast extract for the assay of N-myristoylglycylpeptide synthetase activity. Yeast cultures were grown as described above to O.D. 660 nm of 1 to 3. Cells from 40 ml of culture were collected by centrifugation at 4° C. at 7600×g for 10 minutes. The supernatant was decanted, the cell pellet was resuspended by pipetting into 1 ml of cold 10 mM Tris, pH 7.4, transferred to a 1.5 ml conical polypropylene centrifuge tube, and the cells were then repelleted at 4° C. at 7600×g for 10 minutes. Cells were resuspended in 400 µl of cold assay lysis buffer (10 mM Tris, pH 7.4, 1 mM dithiothreitol, 0.1 mM ethylene glycol-bis(β-aminoethyl ether) N,N,N',N'-tetraacetic acid (EGTA), 10 µg/ml Aprotinin) by pipetting. Approximately 400 µl of 0.5 mm glass beads were added to the resuspended cells, and the cells were lysed by vortexing as described above for lysis of radioactively labeled cells. After allowing the beads to settle, the lysate was collected and cellular debris was removed by centrifugation at 4° C. at 1000×g for 10 minutes. The supernatant was then centrifuged at 4° C. at 45,000 rpm for 30 minutes in a Beckman 75 Ti rotor. The supernatant was removed, and the crude membrane pellet was resuspended by pipetting into 400 µl of cold assay lysis buffer. Aliquots of the three cellular fractions were either assayed immediately or stored at −60° C. The activity associated with crude membranes was stable at −60° C. for at least 3 months. Protein was determined by the method of Peterson, *Anal. Biochem.* 83, 346–356 (1977).

Assay for N-myristoylglycylpeptide synthetase activity. [$^3$H]Fatty acyl CoA was synthesized enzymatically and added to the incubation as follows. The acyl CoA synthetase reaction consisted of (per one assay tube): 0.5 µCi of [$^3$H]myristic acid; 25 µl of 2× assay buffer (20 mM Tris, pH 7.4, 2 mM dithiothreitol, 10 mM $MgCl_2$, 0.2 mM EGTA); 5 µl of 50 mM ATP in distilled water, adjusted to pH 7.0 with NaOH; 2.5 µl of 20 mM lithium CoA in distilled water; 15 µl of 1mU/µl of Pseudomonas acyl CoA synthetase (Sigma) in 50 mM N-2-hydroxyethylpiperazine-N'-2-ethane sulfonic acid, pH 7.3; 2.5 µl of distilled water. The reaction was allowed to proceed for 20 minutes at 30° C. Typically, 40% to 50% of the [$^3$H]fatty acid was converted to its CoA ester by this procedure as measured by determining the radioactivity remaining in the reaction after acidification with 6 N HCl to pH 2.0 and extraction 6 times with 5 volumes of heptane, a modification of the method of Hosaka et al., *Meth. Enzymol.* 71, 325–333 (1981). Fifty microliters of this reaction were added to tubes containing 40 µl of assay extraction buffer (see above) and 10 µl of 1 mM GlyAsnAlaAlaAlaAlaArgArg. The assay was initiated by the addition of 10 µl of yeast cell extract (typically 50 µg of protein) per tube, followed by incubation at 30° C. for 10 min. The assay was terminated by the addition of 110 µl of methanol and 10 µl of 100% trichloracetic acid (w/v) per tube, followed by cooling ten minutes on ice. Precipitated protein was removed by centrifugation at 8000×g for 3 minutes in a tabletop Eppendorf centrifuge. (Under these conditions, 95 % of synthetic [$^3$H]myristoylpeptide or [$^3$H]palmitoylpeptide remined soluble when added to an assay mixture.) Fifty microliters of the supernatant were mixed with 75 µl methanol and 75 µl of HPLC buffer A, and analyzed by reverse phase HPLC on a 3.9 mm by 30 cm Waters µ-Bondapak $C_{18}$ column using the same HPLC buffers described above, starting at 35% acetonitrile and eluting with a 1% per minute acetonitrile gradient. One minute fractions were collected and the radioactivity in each fraction determined by liquid scintillation counting. [$^3$H]-Myristoyl-GlyAsnAlaAlaAlaAlaArgArg eluted at 24 minutes, while [$^3$H]palmitoyl-GlyAsnAlaAlaAlaAlaArgArg eluted at 30 minutes.

Results

The chemically synthesized standards of [$^3$H]-myristoylglycylpeptide and [$^3$H]palmitoylglycylpeptide prepared as described above were found to elute from the reverse phase HPLC column with 59% and 65% acetonitrile, respectively, under the conditions used for analyzing assay samples. In the cell lysates prepared and fractionated into crude membranes and soluble fractions above, N-Myristoylglycylpeptide synthetase activity was detected in both crude membrane and soluble fractions, with the specific activities of total, soluble, and membrane fractions being 1410, 1320, and 2260 dpm per μg protein per 10 min assay, respectively. From the initial reaction velocities, it was estimated that 65% of the activity resided in the crude membrane fractions.

The enzymatic reaction product and the chemically synthesized standard [$^3$H]-myristoylpeptide were demonstrated to be identical and to contain myristate covalently bound to glycine when analyzed by the reverse phase HPLC as described above.

To demonstrate the specificity of the N-myristoylglycylpeptide synthetase for the peptide substrate, the ability of other glycylpeptides to competitively inhibit acylation of GlyAsnAlaAlaAlaAlaArgArg also was examined. As can be seen in Table I, below, Test 3, 1 mM concentrations of a dipeptide, a tetrapeptide, and a decapeptide had no effect on myristoylation of 18 μM peptide substrate (ca. one-eighth its $K_m$). Thus, the N-myristoylglycylpeptide synthetase exhibits specificity for the novel octapeptide substrate.

TABLE I

Characterization of N—myristoylglycine peptide synthase

| Test | | Rate of Myristoyl-peptide Synthesis DPM × 10³/10 min |
|---|---|---|
| 1 | Control | 111 |
| | ATP | 9 |
| | CoA | 1 |
| 2 | Control | 83 |
| | Heated Membranes (5 min/65°) | 2 |
| 3 | Control | 26.7 |
| | + 1 mM GN | 28.0 |
| | + 1 mM GPRP | 25.6 |
| | + 1 mM GSSKSPKDPS | 27.4 |

Assays were carried out as described above, using crude membrane fractions from yeast with changes as indicated. In Test 1, the dependence of the assay on ATP and CoA was tested in the absence of exogenous fatty acid CoA ligase. In Test 2, it was demonstrated that the yeast enzyme is heat labile, and in Test 3, that addition of other peptides containing N-terminal glycine does not inhibit the reaction which in this test was measured using only 18 μM peptide substrate rather than the usual 90 μM, in order to maximize pssible inhibitory effects.

EXAMPLE 3

Several other peptides illustrating the present invention were synthesized by the solid phase Merrifield procedure essentially as described in Example 1 and then tested for activity as substrates for the myristoylating enzyme from yeast (S. cerevisiae strain JR153). The peptide substrate specificity of the enzyme was tested under the assay conditions described in Example 2 but using 1 μCi of [$^3$H]-myristic acid per assay tube. The yeast enzyme used in this example was partially purified from a crude homogenate of the cultured yeast cells by fractionation with 51-70% (NH$_4$)$_2$SO$_4$ followed by ion exchange column chromatography with DEAE-Sepharose ® CL-6B (Pharmacia) and affinity chromatography with CoA-agarose affinity matrix (Pharmacia). The peptides were characterized kinetically with the respective kinetic data ($K_m$ and $V_{max}$) being shown in Table II, below.

TABLE II

Peptide Substrate Specificity of Yeast Myristoylating Enzyme

| Peptide Sequence | $K_m$ (mM) | Relative $V_{max}$ (%) |
|---|---|---|
| Gly—Asn—Ala—Ala—Ser | 0.9 | 40 |
| Gly—Asn—Ala—Ala—Ala—Ala | 1.3 | 120 |
| Gly—Asn—Ala—Ala—Ala—Ala—Arg—Arg | 0.06 | 100* |
| Gly—Asn—Phe—Ala—Ala—Ala—Arg—Arg | 0.06 | 106 |
| Gly—Gln—Ala—Ala—Ala—Ala—Arg—Arg | 0.07 | 79 |
| Gly—Ser—Ala—Ala—Ala—Ala—Arg—Arg | 1.7 | 50 |
| Gly—Asn—Glu—Ala—Ala—Ala—Arg—Arg | 1.8 | 47 |
| Gly—Asn—Glu—Ala—Ser—Tyr—Pro—Leu | 2.3 | 55 |
| Gly—Ser—Ser—Lys—Ser—Lys—Pro—Lys | 0.04 | 43 |
| Gly—Ala—Gln—Ala—Ala—Ala—Arg—Arg | 1.4 | 72 |
| Gly—Asn—Arg—Ala—Ala—Ala—Arg—Arg | 0.40 | 98 |

*The $V_{max}$ for the preferred octapeptide was 2840 pmol myristoyl peptide formed per minute per mg of the partially purified yeast enzyme.

EXAMPLE 4

Octapeptide substrate specificity of the myristoylating enzyme from BC$_3$Hl murine muscle cells was tested for several octapeptides in a manner analogous to the procedure of Example 2. These mouse muscle cells were cultured in a conventional manner essentially as described by Olson et al., J. Biol. Chem. 258, 2644–2652 (1983). The enzyme assay was carried out on a postnuclear supernatant fraction from an extract of the mouse muscle cells. Fifty microliters of each trichloroacetic acid-methanol assay supernatant was analyzed by the HPLC procedure essentially as described in Example 2. Table III, below, shows the octapeptide substrate specificity in these tests.

TABLE III

Octapeptide Substrate Specificity of BC$_3$Hl Myristoylating Enzyme

| Octapeptide Sequence | Rate of Myris—toylation DPM/10 Minute Assay |
|---|---|
| none (background) | 500–2000 |
| Gly—Asn—Ala—Ala—Ala—Ala—Arg—Arg | 38,131 |
| Gly—Asp—Ala—Ala—Ala—Ala—Arg—Arg | 1,619 |
| Ala—Asn—Ala—Ala—Ala—Ala—Arg—Arg | 466 |
| Gly—Tyr—Ala—Ala—Ala—Ala—Arg—Arg | 1,398 |
| Gly—Ser—Ser—Lys—Ser—Lys—Pro—Lys | 73,788 |

The first and last listed octapeptide in Table III were highly active in comparison to the other three octapeptides which were essentially inactive in comparison to the background DPM (disintegrations per minute).

Standard amino acid abbreviations are used to identify the sequence of the peptides herein as follows:

| Amino Acid | Abbreviation |
|---|---|
| L-Alanine | Ala or A |
| L-Arginine | Arg or R |
| L-Asparagine | Asn or N |
| L-Aspartic acid | Asp or D |
| L-Glutamine | Gln or Q |
| L-Glycine | Gly or G |
| L-Leucine | Leu or L |
| L-Lysine | Lys or K |
| L-Phenylalanine | Phe or F |
| L-Proline | Pro or P |
| L-Serine | Ser or S |
| L-Tyrosine | Tyr or Y |
| L-Valine | Val or V |

Various other examples will be apparent to the person skilled in the art after reading the present disclosure without departing from the spirit and scope of the invention, and it is intended that all such other examples be included in the scope of the appended claims. Thus, variations in the individual amino acids and/or the chain length of the peptides which do not adversely or detrimentally affect their biologic activity as substrates for myristolylating enzymes as defined herein are intended to be included within the scope of the appended claims.

What is claimed is:

1. A peptide substrate for myristoylating enzymes having an amino acid sequence selected from the group consisting of the following sequences or a physiologically acceptable amide or salt derivative thereof:

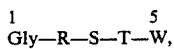

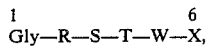

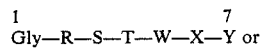

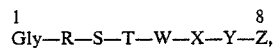

wherein
R=Ala, Asn, Gln or Ser;
S=Ala, Arg, Gln, Glu, Phe or Ser;
T=Ala or Lys;
W=Ala or Ser;
X=Ala, Tyr, or Lys;
Y=Arg or Pro; and
Z=Arg, Leu or Lys.

2. A peptide of claim 1 having the sequence Gly-R-Ala-Ala-Ala-Ala-Arg-Arg wherein R=Asn, Gln or Ser.

3. The peptide of claim 2 wherein R is Asn.

4. The peptide of claim 2 wherein R is Gln.

5. The peptide of claim 1 having the sequence Gly-Asn-Glu-Ala-Ala-Ala-Arg-Arg.

6. The peptide of claim 1 having the sequence Gly-Asn-Glu-Ala-Ser-Tyr-Pro-Leu.

7. The peptide of claim 1 having the sequence Gly-Ser-Ser-Lys-Ser-Lys-Pro-Lys.

8. A peptide of claim 1 having the sequence Gly-R-S-Ala-Ala-Ala-Arg-Arg wherein
R=Ala or Asn and
S=Arg, Gln or Phe.

9. The peptide of claim 8 in which R is Asn and S is Phe.

10. A peptide of claim 1 having the sequence Gly-Asn-Ala-Ala-Ala-Ala.

11. A peptide of claim 1 having the sequence Gly-Asn-Ala-Ala-Ser.

* * * * *